United States Patent [19]
Dyckman et al.

[11] Patent Number: 5,283,376
[45] Date of Patent: Feb. 1, 1994

[54] METHOD OF PHENOL EXTRACTION FROM PHENOL TAR

[75] Inventors: Arkady S. Dyckman; Boris I. Gorovitz; Anatoly M. Somov; Svetlana A. Taranenko; Sergey A. Polyakov, all of St. Petersburg; Alexandr S. Malinovsky, Novokuibyshevsk; Yury I. Petrov, Novokuibyshevsk; Anatoly D. Sorokin, Novokuibyshevsk; Leonty M. Krasnov, Novokuibyshevsk, all of Russian Federation

[73] Assignee: General Electric Co., Pittsfield, Mass.

[21] Appl. No.: 54,663

[22] Filed: Apr. 23, 1993

[51] Int. Cl.$^5$ .................. C07C 37/70; C07C 37/72
[52] U.S. Cl. .................. 568/760; 568/754; 568/761
[58] Field of Search .................. 568/754, 760, 761

[56] References Cited
FOREIGN PATENT DOCUMENTS 0245633 1/1926 United Kingdom ............... 568/760
0457139 11/1936 United Kingdom ............... 568/760

Primary Examiner—Werren B. Lone

[57] ABSTRACT

The invention is related to petrochemistry and is useful in the process of combined production of phenol and acetone by the cumene method. The method is a two stage process which minimizes waste water volume, diminishes equipment corrosion and minimizes consumption of cumene. In the first stage, the phenol tar is treated with a 2-5% water solution of a water soluble amine at a ratio of 1:1.5-1:4.0 to produce two layers, water and organic. At the second stage the water layer from the first stage is thermotreated. As a result, water soluble amino phenate decomposes to amine and phenol. Gaseous amine is removed from the system and then recycled to the first stage. The phenol water solution obtained from the thermotreatment is extracted by standard extraction agents (e.g. diisopropylether, cumene).

The water layer from the phenol extraction is about 50-95% of the original water solution employed in the first stage and is then saturated with the amine and recycled to the first stage.

10 Claims, 1 Drawing Sheet

METHOD OF PHENOL EXTRACTION FROM PHENOL TAR

This invention is related to the field of petrochemical technology, namely, to the production of phenol and acetone by the cumene method.

In the process of producing phenol and acetone from cumene, high boiling by-products are formed, which are usually called phenol tar. Phenol tar contains a great number of components: phenol (PNL), acetophenone (AP), dimethyl phenyl carbinol (DMPC), dimers of alphamethylstyrene, cumylphenols (CP), non-identified products and a small quantity of salt ($Na_2SO_4$) (see Table 1).

TABLE 1

| Average composition of phenol tar | |
|---|---|
| Component | Content, wt % |
| PNL | 10.11 |
| AP | 16.35 |
| DMPC | 8.23 |
| Dimers | 31.99 |
| CP | 24.13 |
| Total non-identified products | 8.11 |
| Salt | 1.08 |

It is estimated that at least 60,000 metric tons of phenol tar are produced each year from a world class sumene method plant. Phenol tar has not been found useful as a chemical feed stream and is mainly used as fuel oil. Nevertheless, at the moment, with the concern for environmental cleanup, use of phenol tar as fuel oil is limited and, as a result, it has no commercial value.

Difficulties during phenol tar incineration are caused primarily by the presence of phenol in the tar. In addition, phenol tar contains up to 8 wt % of phenol which increases the phenol losses in the cumene method and accordingly increases the consumption of cumene to make phenol.

Distillation of the tar does not produce phenol of the necessary purity to be of commercial use. Therefore, if the phenol could be efficiently extracted from the phenol tar valuable phenol could be recovered, cumene losses would be reduced and waste disposal would be minimized.

There is a known method for extraction of phenol from the light oily fraction of those products obtained from the dry distillation of coal. This method extracts the phenol with a water solution of methanol or with water alone. Disadvantages of this method are: large dimensions of the extraction unit, the need to readily control the conditions of the processes, temperature of 160° C. and a pressure of 2MPa, and the inability to recover high purity phenol.

Another known method of extraction of phenol from organic mixtures employs the treatment first by an alkaline solution followed by an acid treatment and then extracting by decanting. Disadvantages of this method are mainly large quantities of waste water and high corrosion of equipment.

Separation of pure phenol from phenol tar by rectification where the tar has a relatively low content of phenol compared with acetophenone is restricted by the presence of an azeotrope with a boiling point maximum for the phenol-acetophenone mixture. Still another known method of phenol extraction, in particular paracumylphenol, from phenol tar is by the treatment of the tar by an alkaline water solution followed by further treatment of the water layer with a solution of strong mineral acid to neutralize the water layer followed by the separation of the layers. Disadvantages of this method are the large volume of chemically polluted waste waters and equipment corrosion.

SUMMARY OF THE INVENTION

The present invention separates pure phenol from phenol tars, using a liquid-liquid extraction obtaining phenol tar free of phenol, reducing the quantity of waste water, reducing consumption of cumene and avoiding the build up of salt in the phenol tar.

The above mentioned results are reached by the following method.

The present method of phenol tar processing includes interaction of phenol tar with a water amine solution which when in contact with the tar forms an aminophenate, liberation of phenol by thermal decomposition of the aminophenate, and extraction of the phenol from the water solution followed by the separation of phenol from the extracting agents.

DETAILED DESCRIPTION OF THE INVENTION

Figure 1:
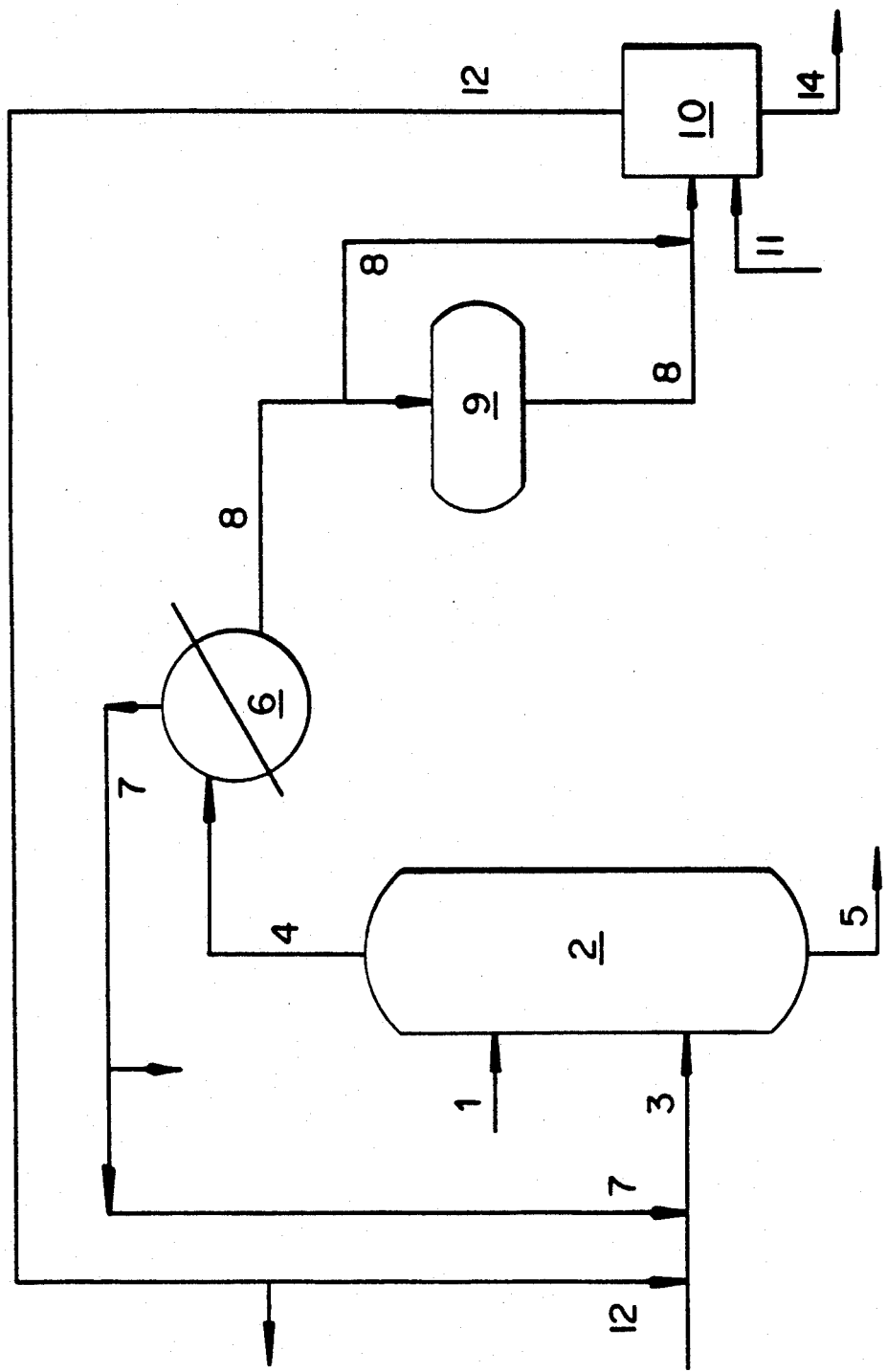
FIG. 1 is a simplified process flow chart of the process of the present invention.

The first stage of the process is the treatment of the phenol tar with a 1-10 weight %, preferably 2-5%, water solution of a water soluble amine. A typical such water soluble amine has the formula $NR_3$ wherein each R is independently alkyl or hydrogen, preferably alkyl of from one to three carbon atoms or hydrogen, and most preferably hydrogen. Examples of amines useful in the present invention are ammonia, methyl amine, ethyl amine, propyl amine, dimethylamine, diethyl amine, dipropyl amine, trimethyl amine, triethyl amine, tripropyl amine and methyl ethyl amine. The phenate formed is transferred to the water phase. The phenol tar purified by this method can be processed to extract pure acetophenone, sent to catalytic decomposition, or to incineration.

In the second stage of the process, aminophenate undergoes thermal decomposition. The amine formed is recycled and the phenol containing water solution goes to extraction performed in the usual way. Suitable extracting agents include ethers, hydrocarbons and cumene. After extraction 30-98 volume %, preferably 50-95% of the water solution is contacted with a water soluble amine to give the appropriate water amine solution and the resulting solution is then recycled for contact with additional phenol tar.

The distinctive features of the present method are that the alkaline agent is an amine solution at a volume ratio of phenol tar/water amine solution equal to 1:1-8, preferably 1:1.5-4; that the phenol is recovered by the thermal decomposition of aminophenate and that 30 to 98% of the volume of water is recycled after phenol extraction back to the first state of the phenol tar extraction process.

To realize the method according to suggested invention water solutions of a water soluble amine of 1 to 10% are used. Lowering the amine concentration below 1%, leads to increase of reaction volumes and increase of concentration above 10% worsens the separation between water and organic phases.

With an increase of recycle over 98%, the degree of salt extraction decreases. Lowering the recycle below 30% increases the quantity of water included in the process.

Advantages of the present method over known methods include the following:

1. The present method practically substantially reduces consumption of reagents (minimum consumption is determined only by technological losses).
2. In the process performed by the present method the quantity of waste water is reduced.
3. As acids are not present, corrosion of equipment is minimal.
4. No emulsions are formed during the stages of the process.

FIG. 1 sets forth a flow diagram of an illustrative embodiment of the process of the present invention. In this invention a phenol tar stream (1) enters the upper portion of an extractor (2) which typically may be a counter current distillation column and may contain a suitable packing or trays and downcomers. Other suitable vessels may be employed to carry out this extraction since the design of the extractor is not critical to the present invention. An aqueous amine stream (3) enters the lower portion of the extractor (2). The phenol tar undergoes treatment by the amine from the aqueous amine stream to form aminophenate. This treatment stage is referenced previously as the first stage of the process. The aminophenate stream (4) exits the top portion of the extractor (2) and a tar stream (5) from which phenol has been removed exits the bottom portion of the extractor (2) and is disposed of efficiently as waste, is employed for a suitable use for heavy tars or is extracted to remove contained acetophenone.

The aminophenate stream (4) enters a thermal decomposing vessel (6). The vessel may be of any suitable configuration for raising the temperature of the aminophenate above the decomposition temperature of aminophenate to produce the water soluble amine and phenol. This decomposition is a well known chemical reaction which proceeds without a catalyst but may employ a suitable catalyst to promote decomposition of the aminophenate at a lower temperature as is taught in the prior art. An amine stream (7) exits the top portion of the vessel and may be used as a raw material in a different process or, preferably, to be employed in making up the aqueous amine stream (3). The remaining impure phenol/water stream (8) exits the decomposer (6) and enters a hold tank (9) or bypasses the hold tank (9) and directly enters a phenol extractor (10). A stream of a suitable solvent (11), which may employ any suitable solvent for extraction of phenol from water in the phenol extractor (10), enters the phenol extractor (10). Preferred solvents are diisopropylether, cumene as well as other known hydrocarbon or ether solvents for phenol. Selection of the solvent will primarily depend on economic availability at the site of the process of this invention. A water stream (12) is recovered from the phenol extractor (10) and returned to make up the aqueous water soluble amine stream (3), sent to another use or disposed of as a waste. The phenol/solvent stream (14) exits the phenol extractor (10) for separation of the phenol from the solvent or for use as raw material. If the solvent is separated from the phenol, the solvent may be recycled to solvent stream (11). The decomposition of aminophenate and the extraction of phenol from the impure phenol/water stream is previously referenced as the second stage of the process.

The present invention is further illustrated by the following non-limiting examples.

EXAMPLE 1

30 g of phenol tar is mixed with 45 ml of a 3% solution of ammonia (ratio phenol tar/water=1:1.5). Stirring is performed for 1 hour. After stirring, the mixture is allowed to stand for 45 mins in a separating funnel. After that period of time, the organic layer is separated from the three water layer. This operation is performed two more times. The water layers are combined after the washing and boiled for 4 hours in a round bottom flask under reflux for decomposition of ammonium phenate to phenol and ammonia. The ammonia obtained after decomposition is used for further washings. From the water layer after cooling phenol is extracted with diisopropylether and later the phenol is separated by distillation from the extraction agents. 50% of the water obtained from the phenol extraction is used again for phenol extraction from phenol tar. The experimental results are given in Table 2.

EXAMPLE 2

This experiment is performed in the same way as described in Example 1, the difference being that the phenol tar/water ratio is 1 to 4 and 95% of the water obtained after extraction of phenol is recycled. The results of this experiment are given in Table 2.

The present process allows the separation of up to 95% of phenol contained in phenol tar and lowers the salt content by almost three orders of magnitude which improves the quality of the remaining phenol tar.

One distinctive feature of the invention is the range of ratios of phenol tar/water ammonia solution of 1/1-⅛, preferably 1/1.5-1/5.4. The increase of this ratio leads to the increase of reaction volume and some decrease of the extracted phenol quantity. Lowering this ratio below 1 leads to a poorer separation of water and organic phase and the potential for emulsion formation.

Another distinctive feature of this method is the recycle of 50 to 95% of the water obtained from the second stage phenol extraction to the first stage contact with phenol tar after preliminary saturation by ammonia.

TABLE 2

| Experimental results Phenol extraction from phenol tar | | |
|---|---|---|
| Experiment No. | 1 | 2 |
| Extraction of phenol from phenol tar, rel % | 95.0 | 95.4 |
| Salt content in phenol tar after washing, wt % | 0.004 | 0.003 |
| Phenol extraction with diisopropylether after decomposition of ammonium phenate, rel % | 95.0 | 94.8 |

What is claimed as the present invention is:

1. A method of extracting phenol from the phenol tar byproduct of a process for producing phenol from cumene which comprises
   a) preparing an amine water solution,
   b) contacting the phenol tar with the amine water solution to form aminophenate in the water solution,
   c) heating the water solution of amino phenate to decompose the aminophenate into amine and phenol.
2. The method of claim 1 wherein the amine water solution is prepared by dissolving the amine in water.

3. The method of claim 2 wherein the phenol is separated from the water and the water thus obtained is used to prepare the amine water solution.

4. The method of claim 1 wherein the volume ratio of phenol tar to amine in the water amine solution is from about 1 to 1 to about 1 to 8.

5. The method of claim 1 wherein the water amine solution comprises from about 1 weight percent amine to about 10 weight percent amine.

6. The method of claim 1 wherein the phenol is separated from the water, a portion of the water is saturated with the amine and the phenol tar is contacted with the water amine solution.

7. The method of claim 6 wherein the portion of water is from about 30 to about 98% of the water from which phenol is separated.

8. The method of claim 1 wherein the amine is of the formula $NR_3$ wherein R is alkyl or hydrogen.

9. The method of claim 8 wherein R is hydrogen.

10. The method of claim 3 wherein the amine is ammonia.

* * * * *